United States Patent [19]
Killion

[11] Patent Number: 4,763,753
[45] Date of Patent: Aug. 16, 1988

[54] INSERT EARPHONES FOR AUDIOMETRY

[75] Inventor: Mead C. Killion, Elk Grove Village, Ill.

[73] Assignee: Etymotic Research, Inc., Elk Grove Village, Ill.

[21] Appl. No.: 784,285

[22] Filed: Oct. 4, 1985

Related U.S. Application Data

[63] Continuation-in-part of Ser. No. 628,009, Jul. 5, 1984, Pat. No. 4,677,679.

[51] Int. Cl.⁴ .................. H04R 25/04; H04R 1/10; H04R 1/28
[52] U.S. Cl. ................... 181/130; 381/68.2; 381/68.6; 381/159; 381/187
[58] Field of Search ............ 179/180, 107 R, 107 FD, 179/178, 179, 156 R, 182 R; 181/131, 130, 137; 381/158, 159, 187, 68, 68.1, 68.2, 68.6

[56] References Cited

U.S. PATENT DOCUMENTS

| | | | |
|---|---|---|---|
| 1,629,100 | 5/1927 | Hartley | 381/98 |
| 1,757,938 | 5/1930 | Hayes | 381/158 |
| 2,389,868 | 11/1945 | Olson | 181/131 |
| 3,835,263 | 9/1974 | Killion | 381/68.2 |
| 4,006,321 | 2/1977 | Carlson | 381/158 |
| 4,090,040 | 5/1978 | Berland | 381/68.2 |
| 4,167,223 | 9/1979 | Liesse | 381/158 |
| 4,189,627 | 2/1980 | Flanagan | 381/158 |
| 4,270,627 | 6/1981 | Hill | 181/131 |
| 4,677,675 | 6/1987 | Killion et al. | 381/68.2 |
| 4,677,679 | 6/1987 | Killion | 381/68.6 |

Primary Examiner—Jin F. Ng
Assistant Examiner—Danita R. Byrd
Attorney, Agent, or Firm—Neuman, Williams, Anderson & Olson

[57] ABSTRACT

Earphones especially adapted for use in audiometry have electroacoustical transducer elements located at a distance from the ear and incorporate coupling paths and chambers so arranged as to eliminate undesirable resonances and to obtain a smooth and accurate frequency response characteristic.

13 Claims, 2 Drawing Sheets

INSERT EARPHONES FOR AUDIOMETRY

This application is a continuation-in-part of my prior application Ser. No. 628,009, filed July 5, 1984 now U.S. Pat. No. 4,677,679.

This invention relates to earphones and more particularly to earphones which develop a high output while having smooth and accurate frequency response characteristics and while being compact, reliable and manufacturable at relatively low cost. They provide a high degree of noise exclusion, can be comfortably worn for extended periods of time and are especially advantageous in auditory brainstem response (ABR) and other audiometry applications. However, various features of the invention are applicable to other earphone applications including hearing aid applications.

BACKGROUND OF THE INVENTION

In my aforesaid prior application, I disclose earphone apparatus in which an earmold is coupled through a main sound tube to a base unit which is of compact form and which includes a miniature receiver with a sound outlet connected to the end of the main sound tube and also to acoustic resonance cancellation means within the base unit. The base unit also includes an electrical response-equalization network which augments the effect of the acoustic elements to obtain frequency response characteristics which are not obtained with conventional audiometry earphones and which are highly desirable. One characteristic is a substantially flat response over a frequency range extending from less than 50 Hz to more than 10,000 Hz. Another frequency response characteristic obtained is one that closely matches the diffuse-sound-field response of the normal external ear.

SUMMARY OF THE INVENTION

This invention was evolved with the general object of providing improved earphones and particularly to provide earphones which incorporate advantageous features of the earphones of my prior application while having increased sensitivity and output.

A specific object of the invention is to provide earphones which have output and frequency response characteristics substantially like those of conventional earphones while incorporating the advantageous features of the earphones of my aforesaid prior application.

Important aspects of the invention relate to the discovery that although the resonance cancellation means of my prior application has very important advantages from the standpoint of obtaining certain highly desirable frequency response characteristics, losses are produced which make it difficult to obtain output characteristics which are high enough to meet the requirements in certain applications.

It was discovered that some improvement could be obtained by using a receiver having a greater power output, but the maximum output was still less than desired. Then, in experimentation, it was discovered that considerable loss was being produced by the resonance cancellation arrangement of my prior application and that a considerable increase in output could be obtained when the cancellation tube and dampers were removed. However, in conducting frequency response tests, it was found that prominent response peaks were produced at a number of frequencies. Such peaks arise from operation of the main transmission path with a low acoustic impedance at its output end, with peaks being produced at frequencies at which the effective length is equal to an odd number of quarter-wavelengths. With a main tubing length of about 278 mm (10.95 inches), a quite prominent peak was produced at a frequency of approximately 250 Hz. Another peak was produced at a frequency of approximately 750 Hz, of lesser magnitude, but still quite prominent. Peaks produced at higher frequencies were of smaller amplitude, decreasing in amplitude as the frequency was increased.

In accordance with the invention, arrangements are provided which operate to cancel the effect of response peaks while producing a high output and other advantages. A chamber is provided which has a certain acoustical compliance and it is coupled to a point of the main transmission path through a path which has a certain acoustical inertance, the dimensions being such that the reactances of the chamber and coupling path are effectively equal at a peak response frequency to reduce the response thereat. Preferably, the cross-sectional area of the coupling path is small in relation to that of the main transmission path and, in addition to its inertance, the path also has a substantial acoustical resistance and it provides a desired degree of damping, no separate damping elements being required. The chamber and coupling path elements are preferably formed inexpensively by short lengths of tubing and they are of small size and are disposed in a small housing which also contains the receiver and an electrical equalization network.

A further feature relates to the provision of a second chamber and a second coupling path which, in one embodiment of the invention, form part of the first coupling path. In another embodiment, the chambers and associated coupling paths are separate. In both cases, the second chamber and second coupling path provide compliant and mass reactances which are effectively equal at a second peak response frequency, to reduce the response thereat, and the second coupling path provides additional acoustic resistance to provide increased damping.

An additional feature relates to the provision of an electrical equalization circuit which provides a high frequency emphasis discovered to be desirable and also smooths the high frequency response.

This invention contemplates other objects, features and advantages which will become more fully apparent from the following detailed description taken in conjunction with the accompanying drawings.

DESCRIPTION OF PREFERRED EMBODIMENTS

Figure 2:
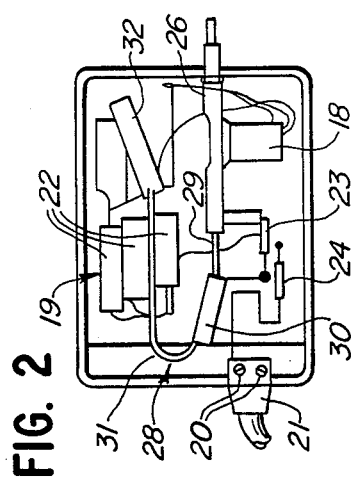
FIG. 2 shows a base unit of the apparatus of FIG. 1, with a cover portion thereof removed.
Figure 1:
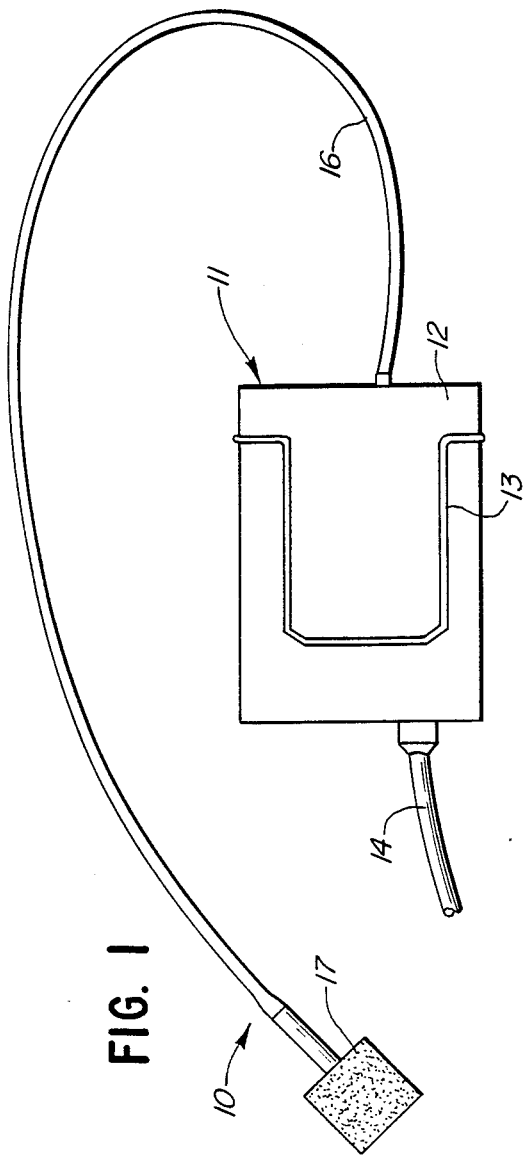
FIG. 1 illustrates the external appearance of an earphone apparatus constructed in accordance with the invention.

Reference numeral 10 generally designates earphone apparatus constructed in accordance with the invention. The apparatus 10 includes a base unit 11 which includes a generally rectangular case 12, with a clip 13 being provided for convenient attachment to the collar of a shirt or blouse. The base unit 11 is connected through a cable 14 to a signal generator or other source of audio signals but it will be understood that a signal generator may be incorporated within the base unit 11 to be energized by a battery within the base unit 11 or from an external supply voltage source.

The base unit 11 is connected through a main sound tube 16 to an ear piece 17 which is designed to be inserted into the end of the ear canal to position the end of the tube 16 within the ear canal. It may also serve to provide an acoustical seal.

By way of example, the sound tube 16 may be a length of 278 mm (10.95 inches) of #16 tubing having an inside diameter or "ID" of 1.35 mm, measured from the wall of the housing 12 to the tip of the ear piece 17. This length, in combination with a 12 mm length inside the case, produces an overall length of 290 mm and taking into account the electro-acoustic delays introduced by the unit itself, an acoustic time delay of 1.0 milliseconds is obtained. This is a convenient value for ABR timebase offset calibration. A length of this order of magnitude is desirable to avoid the production of undesirable electromagnetic interference from the electrical currents flowing in the base unit 11. It will be understood, of course, that shorter or longer lengths may be used.

The sound tube 16 is conveniently made from PVC tubing and the ear plug 17 may be made from slow-recovery foam plugs attached thereto.

As shown in FIG. 2, the base unit 11 includes therewithin a receiver 18 which is connected to an electrical equalization network generally designated by reference numeral 19, the network 19 being connected to spring terminals 20 engageable with pins of a plug 21 at the end of the electrical cable 14. The network 19 includes capacitors 22 and resistors 23 and 24 which are mounted on a circuit board 25 within the base unit 11.

The acoustic output of the receiver 18 is coupled to an intermediate point of a coupling 26 of generally tubular form which is connected to the end of the tubing 16 through a fitting 27 mounted in a wall portion of the housing 12. The opposite end of the coupling 26 is connected to a resonance cancellation assembly of the invention, generally designated by reference numeral 28.

The resonance cancellation assembly 28 includes a tubing section 29 extending from the end of the coupling 16 to one end of a tubing section 30, and a tubing section 31 extending from the opposite end of the section 30 to one end of a section 32 which has an opposite closed end. The tubing section 29 defines a coupling path, the cross-sectional area of which is a small fraction of the area of the main path defined by the main tubing 16 and the passage within the coupling 26. It acts as an acoustic mass or inertance and it also provides an acoustic resistance. The tubing section 30 provides a chamber which has a relatively large volume, in relation to that provided by the tubing section 29, and the chamber within section 30 acts as an acoustic compliance.

At a certain frequency, the inertance of section 29 and the compliance of section 30 combine to provide a series resonance which appears in shunt relation to the flow of signal energy and effectively removes an undesirable resonance peak at that frequency.

Similarly, the passage within tubing section 31 has a small cross-sectional area and the chamber within tubing section 32 has a relatively large volume, such elements operating respectively as an acoustical inertance and an acoustical compliance. At another frequency, the total mass or inertance of tubing sections 29 and 31 combined with the compliance of the chambers of sections 30 and 32, are in series resonance, appearing in shunt relation to the flow of signal energy, effectively removing a second undesirable resonance peak.

The lengths and diameters of the sections are such as to provide acoustic resistances which absorb energy at the frequencies of the undesired peaks and which smooth the overall frequency response. No separate damping element is required and optimum results may be obtained with elements of relatively small size, installed in a compact base unit, as shown.

Figure 3:
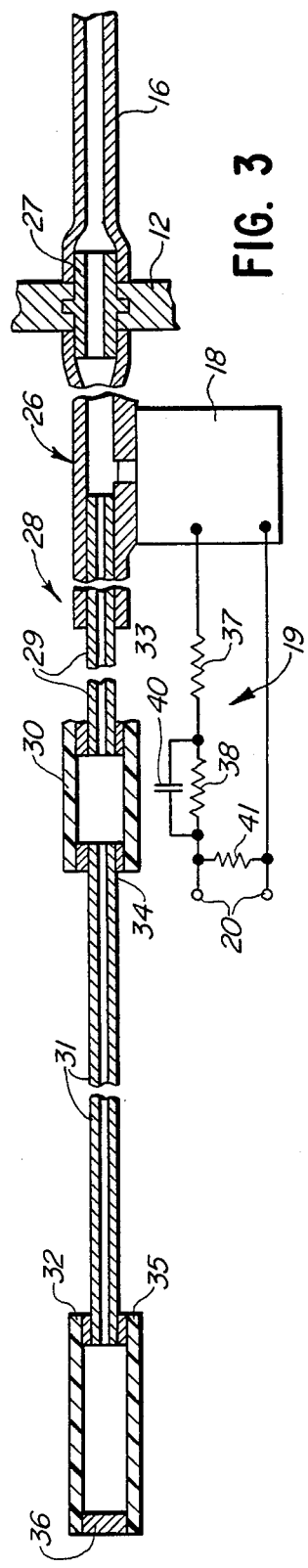
FIG. 3 shows the acoustic elements of the apparatus, in cross-section and on an enlarged scale, as they might appear before installation, and also shows a schematic diagram of an electrical equalization network.

As is shown in FIG. 3, the tubing sections are readily provided from standard types of tubings. As shown, reducers 33 and 34 are provided between the ends of the tubing section 30 and the tubing sections 29 and 31 and a sleeve element 35 is provided between the end of the tubing section 31 and the tubing section 32. A simple plug 36 is inserted in the opposite end of the tubing section 32.

FIG. 3 also shows a schematic diagram of the electrical equalization network 19 which includes resistors 37 and 38 between one of the input terminals and one terminal of the receiver 18, a capacitor 40 in parallel with the resistor 38 and a resistor 41 connected across the input terminals 20. The circuit operates to enhance the high frequency response characteristics in relation to the low frequency response characteristics, such being found to be desirable for optimum results. Resistors 38 and 41 correspond to resistors 23 and 24 of FIG. 2 and capacitor 40 corresponds to capacitor(s) 22. Resistor 37 is not used in the embodiment of FIG. 2.

In the arrangement of FIG. 3, the tubing sections 29 and 30 provide part of a coupling path between the main path and the chamber of section 32, the remainder of that path being provided by tubing section 31.

Figure 4:
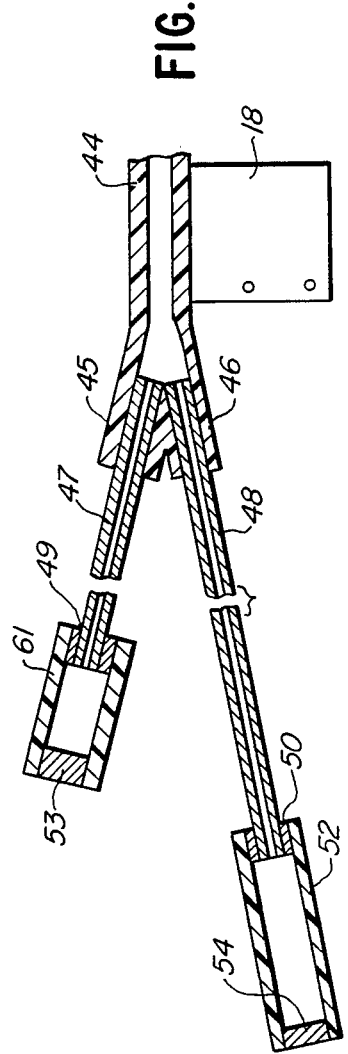
FIG. 4 is a view similar to part of FIG. 3, showing a modification.

FIG. 4 shows a modification in which separate paths are provided to two chambers. As shown, the coupling 26 is replaced by a coupling 44, a Y-type fitting at one end with two legs 45 and 46, leg 45 being connected to a tubing section 47 and leg 46 being connected to a tubing section 48, with the opposite ends of sections 47 and 48 being connected through sleeve elements 49 and 50 to large-diameter tubing sections 51 and 52 which have opposite closed ends, plugs 53 and 54 being inserted therein. In this modification, sections 47 and 51 serve the same function as sections 29 and 30 of the FIG. 3 embodiment, while sections 48 and 52 serve the same function as served by the combination of the coupling path sections 29, 30 and 31 and the chamber of section 32. Thus, what may be described as a "parallel" relationship is obtained, as contrasted with a "series" relationship obtained with the FIG. 3 embodiment.

To obtain resonance cancellations at additional frequencies, additional chambers and coupling paths may be provided, by providing additional chambers and coupling paths in series relationship or with a combination of series and parallel relationships. It is also possible to provide arrangements using chamber and coupling path combinations which operate at the same frequency, to provide enhanced attenuation at that frequency, for example.

Figure 5:
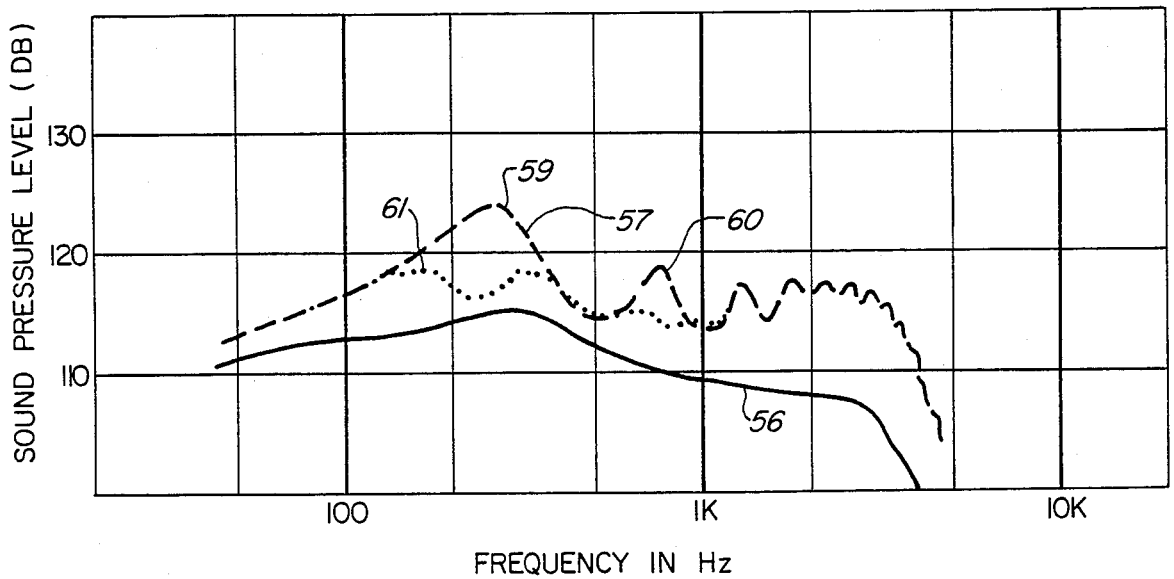
FIGS. 5 and 6 are graphs showing frequency response curves for explanation of the operation of the apparatus and for showing the results obtained therefrom.

The operation of the arrangements of the invention may be clarified by consideration of the frequency response curves of FIG. 5. The solid line curve 56 was obtained with an arrangement as disclosed in my aforesaid prior application, using an auxiliary sound tube and dampers as disclosed therein. The dashed line curve 57 shows the response characteristic obtained with auxiliary sound tube and dampers removed from the arrangement of my aforesaid application or with the resonance cancellation assembly 28 removed from the arrangement as shown in FIG. 3 of this application. A much higher sound pressure level is obtained but prominent peaks 59 and 60 are produced at frequencies of about 250 and 750 Hz and a series of less prominent peaks are obtained at higher frequencies. As aforementioned, such peaks are produced at frequencies at which the effective length is equal to an odd number of quarter wave lengths, a main tubing length of 278 mm (10.95 inches) being effective to produce prominent peaks at 250 and 750 Hz, corresponding to one quarter and three quarter wavelengths.

Dotted line curve 61 shows the response obtained with the arrangement of the invention. Cancellation of the peak 59 is obtained from the operation of the chamber within tubing section 32 which forms a first chamber, in combination with the coupling path through the sections 31, 30 and 29 which forms a first coupling path. Cancellation of the peak 60 is obtained through the operation of the chamber within tubing section 30 in combination with the coupling path through section 29. The chamber within tubing section 30 forms a second chamber and the coupling path through section 29 forms a second coupling path which is included in the aforementioned first coupling path, wherein the first coupling path also includes the additional path in the tubing section 31 between the two chambers. The acoustic resistances in sections 29 and 31 provide a substantial degree of damping at the peaks 59 and 60, while the increase in resistance with frequency that occurs in small tubes aids to prevent any loss of output at higher frequencies. (Such acoustic resistance varies inversely as the square of cross-sectional area and in proportion to the square root of frequency, at higher frequencies). The electrical equalization network 19 operates to enhance the high frequency response in terms of smoothness and level relative to the low frequency response.

Figure 6:
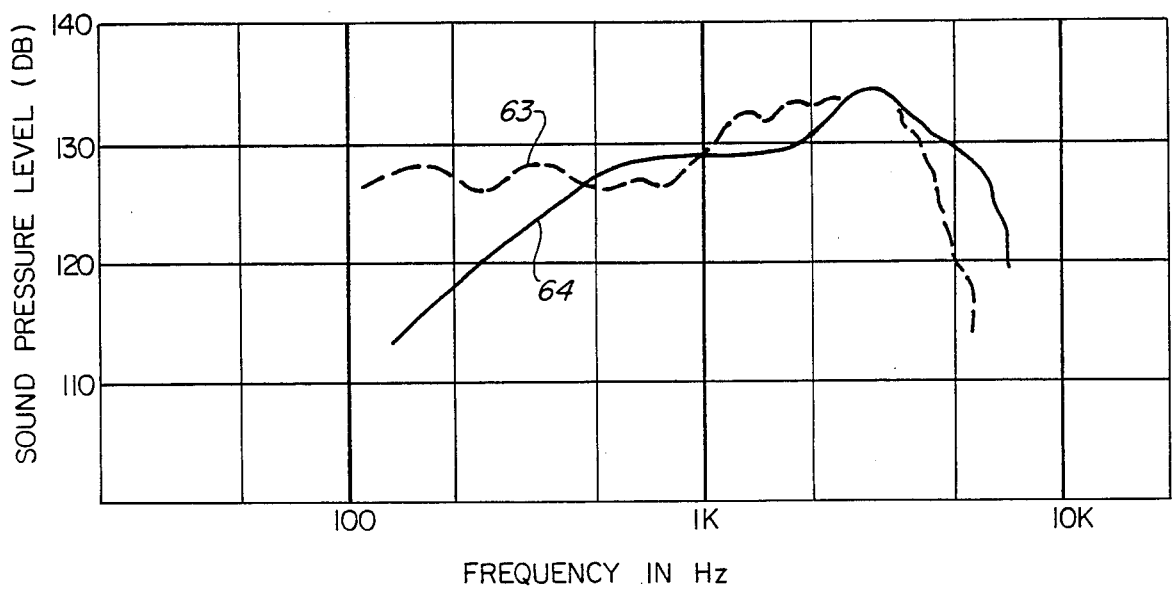

The overall result is a smooth high amplitude response which is highly desirable in certain applications. In FIG. 6, the response of an apparatus constructed in accordance with the invention, shown by a broken line curve 63, is compared with the response characteristic of a commonly used audiometric earphone, shown by the solid line curve 64. A close correlation is obtained, especially in the most important part of the spectrum, from about 500 Hz to about 3000 Hz. Thus, the apparatus of the invention may be used as a "plug-in replacement" of such commonly used earphones while avoiding the disadvantages of such earphones.

By way of example and not by way of limitation, the passages and chambers provided by the tubing sections 29, 30, 31 and 32 may have lengths and inside diameters as follows:

| Section | Length | Diameter |
|---------|--------|----------|
| 29 | 22 mm | .56 mm |
| 30 | 7 mm | 3.8 mm |
| 31 | 43 mm | .56 mm |
| 32 | 14 mm | 3.8 mm |

The coupling 26 which may preferably be of silicon rubber, may have an inside diameter of 1.35 mm, about equal to that of the tubing 16.

Similar dimensions may be used in the FIG. 4 embodiment in which the diameter and length of the passage of section 47 may be the same as that of the section 29 and the length and diameter of the chamber within section 51 may be the same as with respect to section 30. The section 52 may have the same inside diameter as sections 30 and 32 and length about the same as the sum of the length of sections 30 and 32. The tubing section 48 may have an inside diameter which is the same as that of the sections 29 and 31 but its overall length should be about the same as the overall length of the sections 29 and 31.

The optimum dimensions in any particular application are those which operate to remove undesired resonant peaks and which provide a smooth response. Generally speaking, the proper relationship between the acoustic inertances, compliances and resistances is obtained when the following conditions are met simultaneously:

1. The effective inertances and compliances cooperate to produce a minimum of impedance at each of the frequencies at which a peak in the response is to be smoothed, 2. The effective value of the resistance acting at each such frequency is chosen to produce the desired reduction in response level, and 3. The absolute magnitude of the inertances and compliances are chosen to provide the appropriate acoustic impedance level in the region above and below each such frequency in order to provide the desired overall response shape. Since the acoustic compliances, inertances, and mass can be chosen independently (the acoustic compliance is proportional to the volume of a chamber, the inertance is proportional to the ratio of the length to the cross-sectional area of a sound passage, and the resistance is proportional to the ratio of the length to the area squared of the sound passage), the above conditions can be met.

With respect to the electrical equalization network 19, the components may have values as follows:

| Component | Value (300 OHM Nominal Impedance) | Value (10 OHM Nominal Impedance) |
|-----------|-----------------------------------|----------------------------------|
| 37 | 150 OHMS | 0 |
| 38 | 680 OHMS | 27 OHMS |
| 40 | .12 Microfarads | 3.0 Microfarads |
| 41 | 470 OHMS | 13 OHMS |

To obtain a 300 OHM nominal electrical input impedance, a Knowles type CI-1960 receiver may be used with connection to the full winding, while for the 10 OHM nominal impedance, a Knowles type CI-1955 receiver may be used, with connection to one-half the winding.

It will be understood that modifications and variations may be effected without departing from the spirit and scope of the novel concepts of the invention.

I claim:

1. Earphone apparatus for delivering acoustic stimuli to the eardrum of an ear including electrically energized transducer means positioned at a distance from the ear, and sound transmission means defining a main sound transmission path extending from said transducer means to the eardrum, said main sound transmission path having resonance characteristics such as to produce a relatively high amplitude resonant peak response at a certain peak response frequency determined primarily by the length of said main sound transmission path, and resonance cancellation means including a first chamber and first coupling path means in communication between said main transmission path and said first chamber, said first coupling path means including at least one elongated passage having a cross-sectional size and a volume which are small in relation to those of said first chamber to provide an acoustic element having a relatively high acoustic inertance while said first chamber provides an acoustic element having a relatively high acoustic compliance, the acoustical inertance of said first coupling path and said relatively high acoustical compliance of said acoustic element provided by said first chamber being such as to provide a minimum impedance at said certain peak response frequency to reduce the response in said main transmission path at said certain peak response frequency.

2. Earphone apparatus as defined in claim 1, wherein said main transmission path has characteristics such as to produce a second high amplitude peak response at a second peak response frequency also determined by the length of said main sound transmission path, said resonance cancellation means including a second chamber and second coupling path means in communication between said main transmission path and said second chamber, said second coupling path means including an elongated passage having a cross-sectional size and a volume which are small in relation to those of said second chamber to provide an acoustic element having a relatively high acoustic inertance while said second chamber provides an acoustic element having a relatively high acoustic compliance, the acoustic compliance of said second chamber and the acoustic inertance of said second coupling path means being such as to provide relative minimum impedances at the said second peak response frequency to reduce the response at said second peak response frequency in said main transmission path.

3. Earpone apparatus as defined in claim 1 for audiometric applications, wherein said sound transmission means includes an elongated tube having a length such as to position said transducer means at a distance of at least several inches away from the ear to minimize production of electrical fields in the vicinity of the ear by electrical energization of said transducer means.

4. Earphone apparatus as defined in claim 2, wherein said first coupling path means includes said second coupling path means and an additional path means between said second chamber and said first chamber.

5. Earphone apparatus as defined in claim 4, wherein said main transmission path has characteristics such that said second peak response frequency is substantially higher than said first peak response frequency, said first chamber having a volume which is substantially greater than that of said second chamber and having a correspondingly greater acoustical compliance.

6. Earphone apparatus as defined in claim 2, wherein said first and second coupling means communicate independently with said main transmission path.

7. Earphone apparatus as defined in claim 1, wherein said elongated passage of first coupling path has a small cross-sectional area to provide a high acoustical resistance and to provide substantial damping at said first peak response frequency.

8. Earphone apparatus as defined in claim 1, including a housing enclosing said transducer means, means within said housing defining said first chamber and said first coupling path, a tube defining a principal portion of said main transmission path and having one end connected to said housing and an opposite end for coupling to an ear canal, and coupling means within said housing defining a small portion of said main transmission path and coupled to said one end of said tube and also coupled through said first coupling path to said first chamber.

9. Earphone apparatus as defined in claim 2 for audiometric applications, wherein said sound transmission means includes an elongated tube having a length such as to position said transducer means at a distance from the ear to minimize production of electrical fields in the vicinity of the ear by electrical energization of said transducer means and wherein said elongated tube operates to produce peak resonances at frequencies at which the effective length of said tube is equal to an odd number of quarter wavelengths, said first chamber and said first coupling path being effective to reduce the response at the frequency at which the effective length of the tube is equal to one quarter wavelength, said second chamber and said second coupling path being effective to reduce the response at a frequency at which the effective length of said tube is equal to three quarter wavelengths.

10. Apparatus as defined in claim 1, operable as an insert earphone for audiometric applications and including an electrical equalization network associated with said transducer and cooperating with said sound transmission means to obtain an overall frequency response characteristic closely approximating that of a conventional audiometric headphone through at least that portion of the spectrum which extends from about 500 Hz to 3000 Hz.

11. Apparatus as defined in claim 1, wherein said certain peak response frequency is that at which the length of said main transmission path is approximately one-fourth of a wavelength.

12. Earphone apparatus as defined in claim 11, wherein said main transmission path has characteristics such as to produce a second high amplitude peak response at a second peak response frequency at which the length of said main transmission path is approximately three-fourths of a wavelength, said resonance cancellation means including a second chamber and second coupling path means in communication between said main transmission path and said second chamber, said second coupling path means including an elongated passage having a cross-sectional size and a volume which are small in relation to those of said second chamber to provide an acoustic element having a relatively high acoustic inertance while said second chamber provides an acoustic element having a relatively high acoustic compliance, the acoustic compliance of said second chamber and the acoustic inertance of said second coupling path means being such as to provide a relative minimum impedance at the said second peak response frequency to reduce the response at said second peak response frequency in said main transmission path.

13. Apparatus as defined in claim 12, wherein the acoustic resistances of said first and second coupling path means are such as to provide a smooth frequency response characteristic through a frequency range from below said certain peak response frequency to above said second frequency response frequency.

* * * * *